United States Patent
Shannon et al.

(10) Patent No.: US 9,026,371 B2
(45) Date of Patent: May 5, 2015

(54) METHOD FOR CROSS-INSTRUMENT COMPARISON OF GENE EXPRESSION DATA

(75) Inventors: Mark E. Shannon, San Francisco, CA (US); Mark F. Oldham, Los Gatos, CA (US); David W. Ruff, San Francisco, CA (US)

(73) Assignee: Applied Biosystems, LLC, Carlsbad, CA (US)

( * ) Notice: Subject to any disclaimer, the term of this patent is extended or adjusted under 35 U.S.C. 154(b) by 1443 days.

(21) Appl. No.: 12/558,428

(22) Filed: Sep. 11, 2009

(65) Prior Publication Data

US 2010/0036616 A1 Feb. 11, 2010

Related U.S. Application Data

(63) Continuation of application No. 11/086,253, filed on Mar. 22, 2005, now abandoned, which is a continuation-in-part of application No. 10/944,673, filed on Sep. 17, 2004, now abandoned, and a continuation-in-part of application No. 10/944,668, filed on Sep. 17, 2004, now abandoned, which is a continuation-in-part of application No. 10/913,601, filed on Aug. 5, 2004, now Pat. No. 7,233,393.

(60) Provisional application No. 60/504,500, filed on Sep. 19, 2003, provisional application No. 60/504,052, filed on Sep. 19, 2003, provisional application No. 60/589,224, filed on Jul. 19, 2004, provisional application No. 60/589,225, filed on Jul. 19, 2004, provisional application No. 60/601,716, filed on Aug. 13, 2004.

(51) Int. Cl.
*G01N 33/48* (2006.01)
*C40B 30/04* (2006.01)
*G06F 19/20* (2011.01)
*C12Q 1/68* (2006.01)

(52) U.S. Cl.
CPC ............ *C40B 30/04* (2013.01); *C12Q 1/686* (2013.01); *G06F 19/20* (2013.01)

(58) Field of Classification Search
None
See application file for complete search history.

(56) References Cited

U.S. PATENT DOCUMENTS

| | | | |
|---|---|---|---|
| 4,586,546 A | 5/1986 | Mezei et al. | |
| 5,916,524 A | 6/1999 | Tisone | |
| 5,998,768 A | 12/1999 | Hunter et al. | |
| 5,999,209 A | 12/1999 | Hunter et al. | |
| 6,005,664 A | 12/1999 | Korenberg et al. | |
| 6,036,920 A | 3/2000 | Pantoliano et al. | |
| 6,088,100 A | 7/2000 | Brenan et al. | |
| 6,154,707 A | 11/2000 | Livak et al. | |
| 6,203,759 B1 | 3/2001 | Pelc et al. | |
| 6,214,293 B1 | 4/2001 | Pantoliano et al. | |
| 6,235,520 B1 | 5/2001 | Dehlinger et al. | |
| 6,309,608 B1 | 10/2001 | Zhou et al. | |
| 6,358,679 B1 | 3/2002 | Heid et al. | |
| 6,365,375 B1 | 4/2002 | Dietmaier et al. | |
| 6,373,726 B1 | 4/2002 | Russell | |
| 6,448,089 B1 | 9/2002 | Vuong | |
| 6,472,218 B1 | 10/2002 | Stylli et al. | |
| 6,586,257 B1 | 7/2003 | Vuong | |
| 6,632,809 B2 | 10/2003 | Grillot et al. | |
| 6,638,483 B2 | 10/2003 | Vuong | |
| 6,653,300 B2 | 11/2003 | Bebbington et al. | |
| 6,653,301 B2 | 11/2003 | Bebbington et al. | |
| 6,664,247 B2 | 12/2003 | Bebbington et al. | |
| 6,730,883 B2 | 5/2004 | Brown et al. | |
| 6,814,933 B2 | 11/2004 | Vuong | |
| 6,825,927 B2 | 11/2004 | Goldman et al. | |
| 6,852,986 B1 | 2/2005 | Lee et al. | |
| 2001/0049134 A1 | 12/2001 | Lee et al. | |
| 2002/0090320 A1 | 7/2002 | Burow et al. | |
| 2002/0098593 A1 | 7/2002 | Nelson et al. | |
| 2002/0098598 A1 | 7/2002 | Coffen et al. | |
| 2002/0198858 A1 | 12/2002 | Stanley et al. | |
| 2003/0027179 A1 | 2/2003 | Heid et al. | |
| 2003/0087446 A1 | 5/2003 | Eggers | |
| 2003/0100995 A1 | 5/2003 | Loraine et al. | |
| 2003/0108868 A1 | 6/2003 | Richards | |
| 2003/0109060 A1 | 6/2003 | Cook et al. | |
| 2003/0118483 A1 | 6/2003 | Militzer et al. | |
| 2003/0124539 A1 | 7/2003 | Warrington et al. | |
| 2003/0136921 A1 | 7/2003 | Reel | |
| 2003/0179639 A1 | 9/2003 | Bell et al. | |

(Continued)

FOREIGN PATENT DOCUMENTS

| | | |
|---|---|---|
| WO | 94/27719 | 12/1994 |
| WO | 95/11262 | 4/1995 |
| WO | 97/37036 | 10/1997 |
| WO | 01/90951 | 11/2001 |

OTHER PUBLICATIONS

Ogino et al. (Journal of Molecular Diagnostics, Nov. 2002, vol. 4, No. 4, p. 185-190).*

Barker et al. (Genome Research, May 2004, vol. 14, No. 5, p. 901-907).*

Shi et al. (Clinical Chemistry, 2002, The San Diego Conference, vol. 48, No. 11, p. 2088-2091).*

(Continued)

*Primary Examiner* — Pablo S Whaley

(57) ABSTRACT

A method for determining bias across two domains comprising gene expression data. The method can comprise (a) providing a first domain and a second domain; (b) obtaining information indicative of a bias within the first domain; (c) obtaining information indicative of a bias within the second domain; and (d) using the information indicative of the bias within the first domain and the information indicative of the bias within the second domain to produce an indication of bias across the two domains.

7 Claims, 8 Drawing Sheets

(56) References Cited

U.S. PATENT DOCUMENTS

| | | |
|---|---|---|
| 2003/0190652 A1 | 10/2003 | De La Vega et al. |
| 2003/0202637 A1 | 10/2003 | Yang |
| 2003/0205681 A1 | 11/2003 | Modlin |
| 2003/0207464 A1 | 11/2003 | Lemmo et al. |
| 2003/0215957 A1 | 11/2003 | Lemmo et al. |
| 2004/0014238 A1 | 1/2004 | Krug et al. |
| 2004/0018506 A1 | 1/2004 | Koehler et al. |
| 2004/0057870 A1 | 3/2004 | Isaksson et al. |
| 2004/0061071 A1 | 4/2004 | Dorsel |
| 2004/0131505 A1 | 7/2004 | Koeda |
| 2004/0202577 A1 | 10/2004 | McNeil et al. |
| 2004/0203047 A1 | 10/2004 | Caren et al. |
| 2004/0203164 A1 | 10/2004 | Cizdziel et al. |

OTHER PUBLICATIONS

Becker et al. (Applied and Environmental Microbiology, Nov. 2000, p. 4945-4953).*
Akilesh et al. (Genome Research, 2003, vol. 13, No. 7, p. 1719-1727).*
GeneSpring (User Manual, 2004, pp. 1-746).*
ABI PRISM (User Bulletin #2, ABI PRISM 7700 Sequence Detection System; Published Dec. 11, 1997; Updated Oct. 2001).*
Akilesh, et al., *Genome Research*, vol. 13, No. 7, 2003, 1719-1727.
Barker, et al., *Genome Research*, vol. 14, No. 5, 2004, 901-907.
Becker, et al. *Applied and Environmental Microbiology*, 2000, 4945-4953.
Mocellin, et al., *Trends in Molecular Medicine*, vol. 9, No. 5, 2003, 189-195.
Ogino, et al., *Journal of Molecular Diagnostics*, vol. 4, No. 4, 2002, 185-190.
International Search Report for Int'l Appl. No. PCT/US2006/010383 dated Aug. 3, 2007.
Shi, et al., "The San Diego Conference", *Clinical Chemistry*, vol. 48, No. 11, 2002, 2088-2091.
Suzuki, et al., *Applied and Environmental Microbiology*, vol. 62, No. 2, 1996, 625-630.
Yang, et al., "Normalization for cDNA Microarray Data", Jan. 2001, 1-12 SPIE BIOS, San Jose, CA, Jan. 2001, 1-12.

* cited by examiner

METHOD FOR CROSS-INSTRUMENT COMPARISON OF GENE EXPRESSION DATA

CROSS-REFERENCE TO RELATED APPLICATIONS

This application is a continuation of patent application Ser. No. 11/086,253 filed Mar. 22, 2005, which is a continuation-in-part of patent application Ser. No. 10/944,673 filed on Sep. 17, 2004, now abandoned, and patent application Ser. No. 10/944,668 filed on Sep. 17, 2004, now abandoned. Patent application Ser. No. 10/944,673 claims a benefit to U.S. Provisional Application No. 60/504,500 filed on Sep. 19, 2003; U.S. Provisional Application No. 60/504,052 filed on Sep. 19, 2003; U.S. Provisional Application No. 60/589,224 filed Jul. 19, 2004; U.S. Provisional Application No. 60/589,225 filed on Jul. 19, 2004; and U.S. Provisional Application No. 60/601,716 filed on Aug. 13, 2004. Patent application Ser. No. 10/944,668 is a continuation-in-part of patent application Ser. No. 10/913,601 filed on Aug. 5, 2004, now U.S. Pat. No. 7,233,393, and further claims the benefit of U.S. Provisional Application No. 60/504,052 filed on Sep. 19, 2003; U.S. Provisional Application No. 60/589,224 filed Jul. 19, 2004; and U.S. Provisional Application No. 60/601,716 filed on Aug. 13, 2004.

All literature and similar materials cited in this application, including but not limited to, patents, patent applications, articles, books, treatises, and internet web pages, regardless of the format of such literature and similar materials, are expressly incorporated by reference in their entirety for any purpose. In the event that one or more of the incorporated literature and similar materials differs from or contradicts this application, including but not limited to defined terms, term usage, described techniques, or the like, this application controls.

BACKGROUND

Currently, genomic analysis, including that of the estimated 30,000 human genes is a major focus of basic and applied biochemical and pharmaceutical research. Such analysis may aid in developing diagnostics, medicines, and therapies for a wide variety of disorders. However, the complexity of the human genome and the interrelated functions of genes often make this task difficult. There is a continuing need for methods and apparatus to aid in such analysis.

BRIEF DESCRIPTION OF THE DRAWINGS

The skilled artisan will understand that the drawings, described herein, are for illustration purposes only. The drawings are not intended to limit the scope of the present teachings in any way.

DETAILED DESCRIPTION

Figure 1:
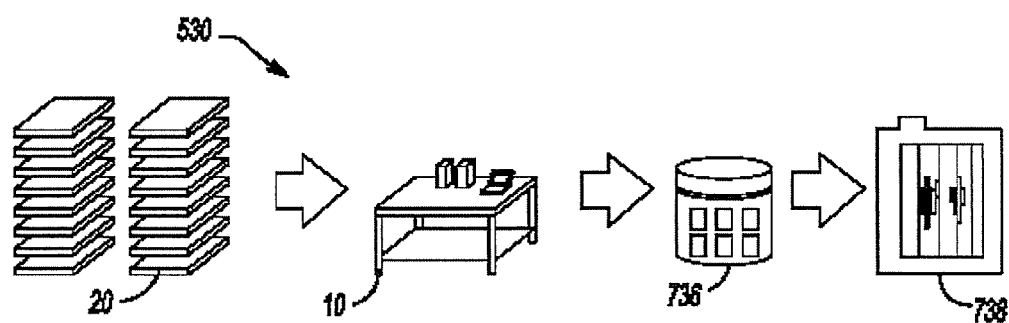
FIG. 1 is a flowchart illustrating the use of a database system according to some embodiments.

The following description of various embodiments is merely exemplary in nature and is in no way intended to limit the present teachings, applications, or uses. Although the present teachings will be discussed in various embodiments as relating to polynucleotide amplification, such as PCR, such discussion should not be regarded as limiting the present teaching to only such applications.

In general, gene expression is a process by which a gene's coded information is converted into the structures present and operating in the cell. Gene expression is a multi-step process that begins with transcription and translation and is followed by folding, post-translational modification and targeting. The amount of protein that a cell expresses depends on the tissue, the developmental stage of the organism and the metabolic or physiologic state of the cell. Expressed genes can include those that are transcribed into mRNA and then translated into protein and those that are transcribed into RNA but not translated into protein. In various embodiments, gene expression can be studied using analytical techniques such as polymerase chain reaction (PCR), Northern blots, serial analysis of gene expression (SAGE) microarrays, hybridization arrays, and high density oligonucleotide arrays.

Briefly, by way of background, PCR can be used to amplify a sample of target Deoxyribose Nucleic Acid (DNA) for analysis. Typically, the PCR reaction involves copying the strands of the target DNA and then using the copies to generate additional copies in subsequent cycles. Each cycle doubles the amount of the target DNA present, thereby resulting in a geometric progression in the number of copies of the target DNA. The temperature of a double-stranded target DNA is elevated to denature the DNA, and the temperature is then reduced to anneal at least one primer to each strand of the denatured target DNA. In some embodiments, the target DNA can be a cDNA. In some embodiments, primers are used as a pair—a forward primer and a reverse primer—and can be referred to as a primer pair or primer set. In some embodiments, the primer set comprises a 5' upstream primer that can bind with the 5' end of one strand of the denatured target DNA and a 3' downstream primer that can bind with the 3' end of the other strand of the denatured target DNA. Once a given primer binds to the strand of the denatured target DNA, the primer can be extended by the action of a polymerase. In some embodiments, the polymerase can be a thermostable DNA polymerase, for example, a Taq polymerase. The product of this extension, which sometimes may be referred to as an amplicon, can then be denatured from the resultant strands and the process can be repeated. Temperatures suitable for carrying out the reactions are well known in the art. Certain basic principles of PCR are set forth in U.S. Pat. Nos. 4,683, 195, 4,683,202, 4,800,159, and 4,965,188, each issued to Mullis et al.

In some embodiments, PCR can be conducted under conditions allowing for quantitative and/or qualitative analysis of one or more target DNA. Accordingly, detection probes can be used for detecting the presence of the target DNA in an assay. In some embodiments, the detection probes can comprise physical (e.g., fluorescent) or chemical properties that change upon binding of the detection probe to the target DNA. Some embodiments of the present teaching can provide real time fluorescence-based detection and analysis of amplicons as described, for example, in PCT Publication No. WO 95/30139 and U.S. patent application Ser. No. 08/235, 411.

In some embodiments, assay can be a homogenous polynucleotide amplification assay, for coupled amplification and detection, wherein the process of amplification generates a detectable signal and the need for subsequent sample handling and manipulation to detect the amplified product is minimized or eliminated. Homogeneous assays can provide for amplification that is detectable without opening a sealed well or further processing steps once amplification is initiated. Such homogeneous assays can be suitable for use in conjunction with detection probes. For example, in some embodiments, the use of an oligonucleotide detection probe, specific for detecting a particular target DNA can be included in an amplification reaction in addition to a DNA binding agent of the present teachings. Homogenous assays among those useful herein are described, for example, in commonly assigned U.S. Pat. No. 6,814,934.

In some embodiments, methods are provided for detecting a plurality of targets. Such methods include those comprising forming an initial mixture comprising an analyte sample suspected of comprising the plurality of targets, a polymerase, and a plurality of primer sets. In some embodiments, each primer set comprises a forward primer and a reverse primer and at least one detection probe unique for one of the plurality of primer sets. In some embodiments, the initial mixture can be formed under conditions in which one primer elongates if hybridized to a target.

In some embodiments for amplification of a polynucleotide, assay can comprise a preamplification product, wherein one or more polynucleotides in an analyte has been amplified prior to being deposited in at least one of the plurality of wells. In some embodiments, these methods can further comprise forming a plurality of preamplification products by subjecting an initial analyte comprising a plurality of polynucleotides to at least one cycle of PCR to form a detection mixture comprising a plurality of preamplification products. The detection mixture of preamplification products can be then used for further amplification using a PCR. In some embodiments, preamplification comprises the use of isothermal methods.

In some embodiments, a two-step multiplex amplification reaction can be performed wherein the first step truncates a standard multiplex amplification round to boost a copy number of the DNA target by about 100-1000 or more fold. Following the first step, the resulting product can be divided into optimized secondary single amplification reactions, each containing one or more of the primer sets that were used previously in the first or multiplexed booster step. The booster step can occur, for example, using an aqueous target or using a solid phase archived nucleic acid. See, for example, U.S. Pat. No. 6,605,452, Marmaro.

In some embodiments, preamplification methods can employ in vitro transcription (IVT) comprising amplifying at least one sequence in a collection of nucleic acids sequences. The processes can comprise synthesizing a nucleic acid by hybridizing a primer complex to the sequence and extending the primer to form a first strand complementary to the sequence and a second strand complementary to the first strand. The primer complex can comprise a primer complementary to the sequence and a promoter region in anti-sense orientation with respect to the sequence. Copies of anti-sense RNA can be transcribed off the second strand. The promoter region, which can be single or double stranded, can be capable of inducing transcription from an operably linked DNA sequence in the presence of ribonucleotides and a RNA polymerase under suitable conditions. Suitable promoter regions may be prokaryote viruses, such as from T3 or T7 bacteriophage. In some embodiments, the primer can be a single stranded nucleotide of sufficient length to act as a template for synthesis of extension products under suitable conditions and can be poly (T) or a collection of degenerate sequences. In some embodiments, the methods involve the incorporation of an RNA polymerase promoter into selected cDNA molecule by priming cDNA synthesis with a primer complex comprising a synthetic oligonucleotide containing the promoter. Following synthesis of double-stranded cDNA, a polymerase generally specific for the promoter can be added, and anti-sense RNA can be transcribed from the cDNA template. The progressive synthesis of multiple RNA molecules from a single cDNA template results in amplified, anti-sense RNA (aRNA) that serves as starting material for cloning procedures by using random primers. The amplification, which will typically be at least about 20-40, typically to 50 to 100 or 250-fold, but can be 500 to 1000-fold or more, can be achieved from nanogram quantities or less of cDNA.

In some embodiments, a two stage preamplification method can be used to preamplify assay in one vessel by IVT and, for example, this preamplification stage can be 100× sample. In the second stage, the preamplified product can be divided into aliquots and preamplified by PCR and, for example, this preamplification stage can be 16,000× sample or more.

In some embodiments, the preamplification can be a multiplex preamplification, wherein the analyte sample can be divided into a plurality of aliquots. Each aliquot can then be subjected to preamplification using a plurality of primer sets for DNA targets. In some embodiments, the primer sets in at least some of the plurality of aliquots differ from the primer sets in the remaining aliquots. Each resulting preamplification product detection mixture can then be dispersed into at least some of a plurality of wells of a microplate comprising an assay having corresponding primer sets and detection probes for further amplification and detection according to the methods described herein. In some embodiments, the primer sets of assay in each of the plurality of wells can correspond to the primer sets used in making the preamplification product detection mixture. The resulting assay in each of the plurality of wells thus can comprise a preamplification product and primer sets and detection probes for amplification for DNA targets, which, if present in the analyte sample, have been preamplified.

Since a plurality of different sequences can be amplified simultaneously in a single reaction, the multiplex preamplification can be used in a variety of contexts to effectively increase the concentration or quantity of a sample available for downstream analysis and/or assays. In some embodiments, because of the increased concentration or quantity of target DNA, significantly more analyses can be performed with multiplex amplified samples than can be performed with the original sample. In many embodiments, multiplex amplification further permits the ability to perform analyses that require more sample or a higher concentration of sample than was originally available. In such embodiments, multiplex amplification enables downstream analysis for assays that could not have been possible with the original sample due to its limited quantity. In some embodiments, the plurality of aliquots can comprise 16 aliquots with each of the 16 aliquots comprising about 1536 primer sets. In such embodiments, a sample comprising a whole genome for a species, for example a human genome, can be preamplified. In some embodiments, the plurality of aliquots can be greater than 16 aliquots. In some embodiments, the number of primer sets can be greater than 1536 primer sets. In some embodiments, the plurality of aliquots can be less than 16 aliquots and the number of primer sets can be greater than 1536 primer sets. For examples of such embodiments, see PCT Publication No. WO 2004/051218 to Andersen and Ruff.

In some embodiments, multiplex methods are provided wherein assay comprises a first universal primer that binds to a complement of a first target, a second universal primer that binds to a complement of a second target, a first detection probe comprising a sequence that binds to the sequence comprised by the first target, and a second detection probe comprising a sequence that binds to a sequence comprised by the second target. In some embodiments, at least some of a plurality of wells of a microplate comprise a solution operable to perform multiplex PCR. The first and second detection probes can comprise different labels, for example, different fluorophores such as, in non-limiting example, VIC and FAM. Sequences of the first and second detection probes can differ by as little as one nucleotide, two nucleotides, three nucleotides, four nucleotides, or greater, provided that hybridization occurs under conditions that allow each detection probe to hybridize specifically to its corresponding detection probe.

In some embodiments, multiplex PCR can be used for relative quantification, where one primer set and detection probe amplifies the target DNA and another primer set and detection probe amplifies an endogenous reference. In some embodiments, the present teaching provide for analysis of at least four DNA targets in each of a plurality of wells and/or analysis of a plurality of DNA targets and a reference in each of a plurality of wells.

In some embodiments, as seen in FIG. 1, a plurality of microplates having assay filled thereon can be analyzed as described herein with sequence detection system, such as a PCR system to generate data. In some embodiments, this data can be stored in a gene expression analysis system database 736. Software can then be used to generate gene expression analysis information 738.

In some embodiments, a gene expression analysis system can utilize computer software that organizes analysis sessions into studies and stores them in database 738. An analysis session can comprise the results of running microplate in sequence detection system. To analyze session data, one can load an existing study that contains analysis session data or create a new study and attach analysis session data to it. Studies can be opened and reexamined an unlimited number of times to reanalyze the analysis session data or to add other analysis sessions to the analysis.

In some embodiments, gene expression analysis system database 736 stores the analyzed data for each microplate run on sequence detection system as an analysis session in database 736. The software can identify each analysis session by marking indicia of the associated microplate and the date on which it was created. Once analysis sessions have been assigned to a study, various functions can be performed. These functions comprise, but are not limited to, designating replicates, removing outliers, filtering data out of a particular view or report, correction of preamplification values via stored values, and computation of gene expression values.

In various embodiments, real time PCR is adapted to perform quantitative real time PCR (qRT-PCR). In various embodiments, two different methods of analyzing data from qRT-PCR experiments can be used: absolute quantification and relative quantification. In some embodiments, absolute quantification can determine an input copy number of the target DNA of interest This can be accomplished by relating a signal from a detection probe to a standard curve. In various embodiments, relative quantification can describe the change in expression of the target DNA relative to a reference or a group of references such as, for an example, an untreated control, an endogenous control, a passive internal reference, an universal reference RNA, or a sample at time zero in a time course study. When determining absolute quantification, the expression of the target DNA can be compared across many samples, for example, from different individuals, from different tissues, from multiple replicates, and/or serial dilution of standards in one or more matrices. In various embodiments of the present teachings, qRT-PCR can be performed using relative quantification and the use of standard curve is not required. Relative quantification can compare the changes in steady state target DNA levels of two or more genes to each other with one of the genes acting as an endogenous reference which may be used to normalize a signal from a sample gene. In various embodiments, in order to compare between experiments, resulting fold differences from the normalization of sample to the reference can be expressed relative to a calibrator sample. In some embodiments, the calibrator sample is included in each assay 1000. The gene expression analysis system can determine the amount of target DNA, normalized to a reference, by determining $$\Delta C_T = C_{Tq} - C_{Tendo}$$

where $C_T$ is the threshold cycle for detection of a fluorophore in real time PCR; $C_{Tq}$ is the threshold cycle for detection of a fluorophore for a target DNA in assay 1000; and $C_{Tendo}$ is the threshold cycle for detection of a fluorophore for an endogenous reference or a passive internal reference in assay.

In some embodiments, a gene expression analysis system can determine the amount of target DNA, normalized to a reference and relative to a calibrator, by determining:

$$\Delta\Delta C_T = \Delta C_{Tq} - \Delta C_{Tcb}$$

where $C_{Tq}$ is the threshold cycle for detection of a fluorophore for the target DNA in assay 1000; $C_{Tcb}$ is the threshold cycle for detection of a fluorophore for a calibrator sample; $\Delta C_{Tq}$ is a difference in threshold cycles for the target DNA and an endogenous reference; and $\Delta C_{Tcb}$ is a difference in threshold cycles for the calibrator sample and the endogenous reference If $\Delta\Delta C_T$ is determined, the relative quantity of the target DNA can be determined using a relationship of relative quantity of the target DNA can be equal to $2^{-\Delta\Delta C_T}$. In various embodiments, $\Delta\Delta C_T$ can be about zero. In some embodiments, $\Delta\Delta C_T$ can be less than ±1. In various embodiments, the above calculations can be adapted for use in multiplex PCR (See, for example, Livak et al. Applied Biosystems User Bulletin #2, updated October 2001 and Livak and Schmittgen, Methods (25) 402-408 (2001).

In some embodiments, assay can be preamplified, as discussed herein, in order to increase the amount of target DNA prior to distribution into a plurality of wells of a microplate. In some embodiments, assay can be collected, for example, via a needle biopsy that typically yields a small amount of sample. Distributing this sample across a large number of wells can result in variances in sample distribution that can affect the veracity of subsequent gene expression computations. In such situations, assay can be preamplified using, for example, a pooled primer set to increase the number of copies of all target DNA simultaneously.

In various embodiments, preamplification processes can be non-biased, such that all target DNA are amplified similarly and to about the same power. In such embodiments, each target DNA can be amplified reproducibly from one input sample to the next input sample. For example, if target DNA X is initially present in sample A at 100 target molecules, then after 10 cycles of PCR amplification (1000-fold), 100,000 target molecules should be present. Continuing with the example, if target DNA X is initially present in sample B at 500 target molecules, then after 10 cycles of PCR amplification (1000-fold), 500,000 target molecules should be present. In this example, the ratio of target DNA X in samples A/B remains constant before and after the amplification procedure.

In various embodiments, a minor proportion of all target DNA can have an observed preamplification efficiency of less than 100%. In such embodiments, if the amplification bias is reproducible and consistent from one input sample to another, then the ability to accurately compute comparative relative quantitation between any two samples containing different relative amounts of target can be maintained. Continuing the example from above and assuming 50% reproducible amplification efficiency, if target DNA X is initially present in sample A at 100 target molecules, then after 10 cycles of PCR amplification (50% of 1000-fold), 50,000 target molecules should be present. Further continuing the example, if target X is initially present in sample B at 500 target molecules, then after 10 cycles of PCR amplification (50% of 1000-fold), 250,000 target molecules should be present. In this example, the ratio of template X in samples A/B remains constant before and after the amplification procedure and is the same ratio as the 100% efficiency scenario.

In various embodiments, an unbiased amplification of each target DNA (x, y, z, etc.) can be determined by calculating the difference in CT value of the target DNA (x,y,z, etc.) from the $C_T$ value of a selected endogenous reference, and such calculation is referred to as the $\Delta C_T$ value for each given target DNA, as described above. In various embodiments, a reference for a bias calculation can be non-preamplified, amplified target DNA and an experimental sample can be a preamplified amplified target DNA. In some embodiments, the standard sample and experimental sample can originate from the same sample, for example, same tissue, same individual and/or same species. In various embodiments, comparison of $\Delta C_T$ values between the non-preamplified amplified target DNA and preamplified amplified target DNA can provide a measure for the bias of the preamplification process between the endogenous reference and the target DNA (x, y, z, etc.).

Figure 2:
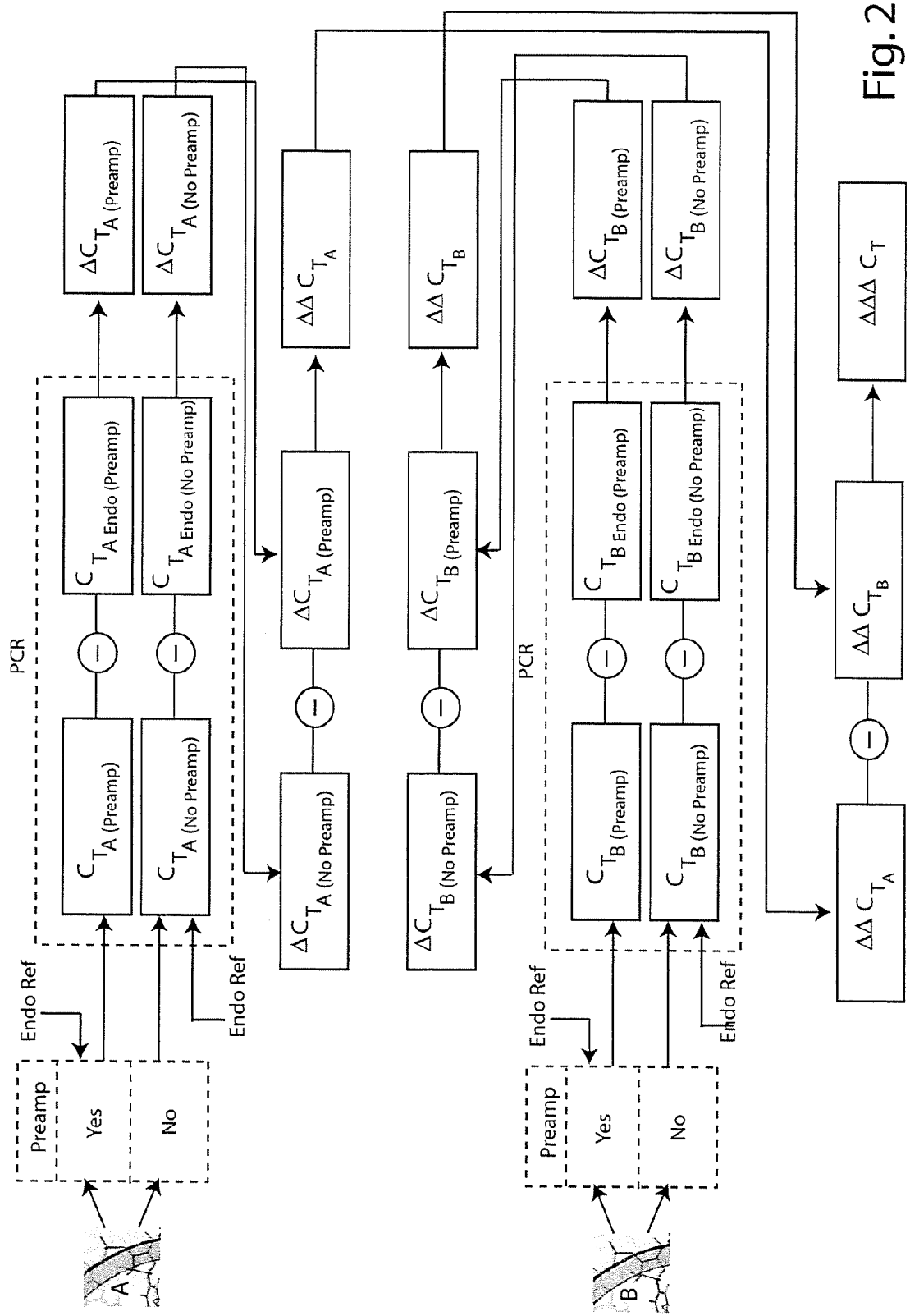
FIG. 2 is a flowchart illustrating a process for determining bias.

In various embodiments, the difference between the two $\Delta C_T$ values ($\Delta \Delta C_T$) can be zero and as such there is no bias from preamplification. This is explained in greater detail below with reference to FIG. 2. In some embodiments, the gene expression analysis system can be calibrated for potential differences in preamplification efficiency that can arise from a variety of sources, such as the effects of multiple primer sets in the same reaction. In some embodiments, calibration can be performed by computing a reference number that reflects preamplification bias. Reference number similarity for a given target DNA across different samples is indicative that the preamplification reaction $\Delta C_T$s can be used to achieve reliable gene expression computations.

In various embodiments of the present teaching, a gene expression analysis system can compute these reference numbers by collecting a sample (designated as Sample A ($S_A$)) and processing it with one or more protocols. A first protocol comprises running individual PCR gene expression reactions for each target DNA ($T_x$) relative to an endogenous reference (endo), such as, for example, 18 s or GAPDH. These reactions can yield cycle threshold values for each target DNA relative to the endogenous control; as computed by:

$$\Delta C_{T\,not\,preamplified}\,T_xS_A = C_{T\,not\,preamplified}\,T_xS_A - C_{T\,notpreamplified}\,endo$$

A second protocol can comprise running a single PCR preamplification step on assay with, for example, a pooled primer set. In various embodiments, the pooled primer set can contain primers for each target DNA. Subsequently, the preamplified product can be distributed among a plurality of wells of a microplate. PCR gene-expression reactions can be run for each preamplified target DNA ($T_x$) relative to an endogenous reference (endo). These reactions can yield cycle threshold values for each preamplified target DNA relative to the endogenous control, as computed by:

$$\Delta C_{T\,preamplified}\,T_xS_A = C_{T\,preamplified}\,T_xS_A - C_{T\,preamplified\,endo}\,T_xS_A$$

A difference between these $\Delta C_T$ not preamplified $T_xS_A$ and $\Delta C_{T\,preamplified}\,T_xS_A$ can be computed by:

$$\Delta\Delta C_T T_xS_A = \Delta C_{T\,not\,preamplified}\,T_xS_A - \Delta C_{T\,preamplified}\,T_xS_A$$

Figure 3:
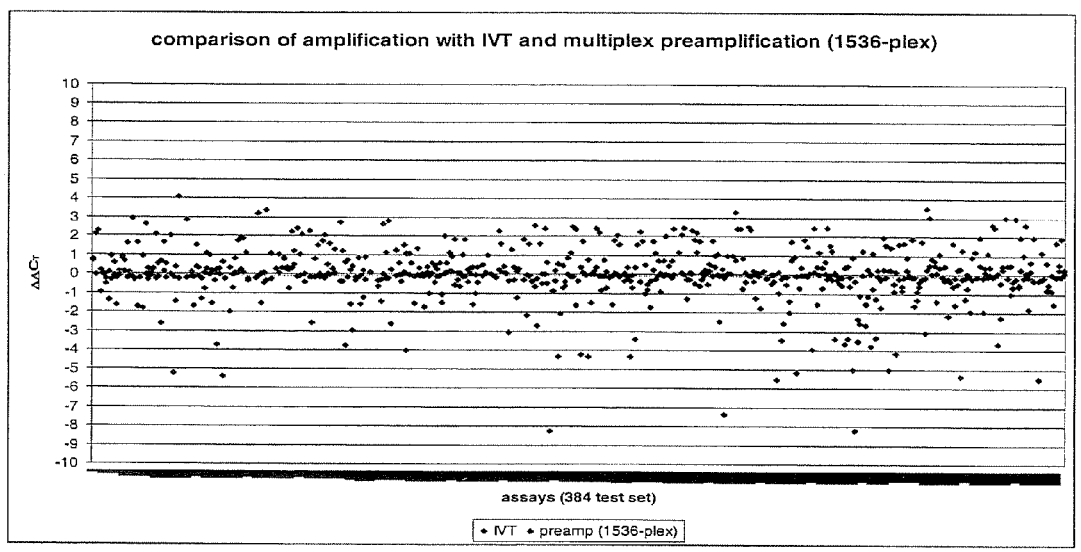
FIG. 3 is a graph exemplifying a comparison of amplification with IVT and multiplex preamplification.
Figure 4:
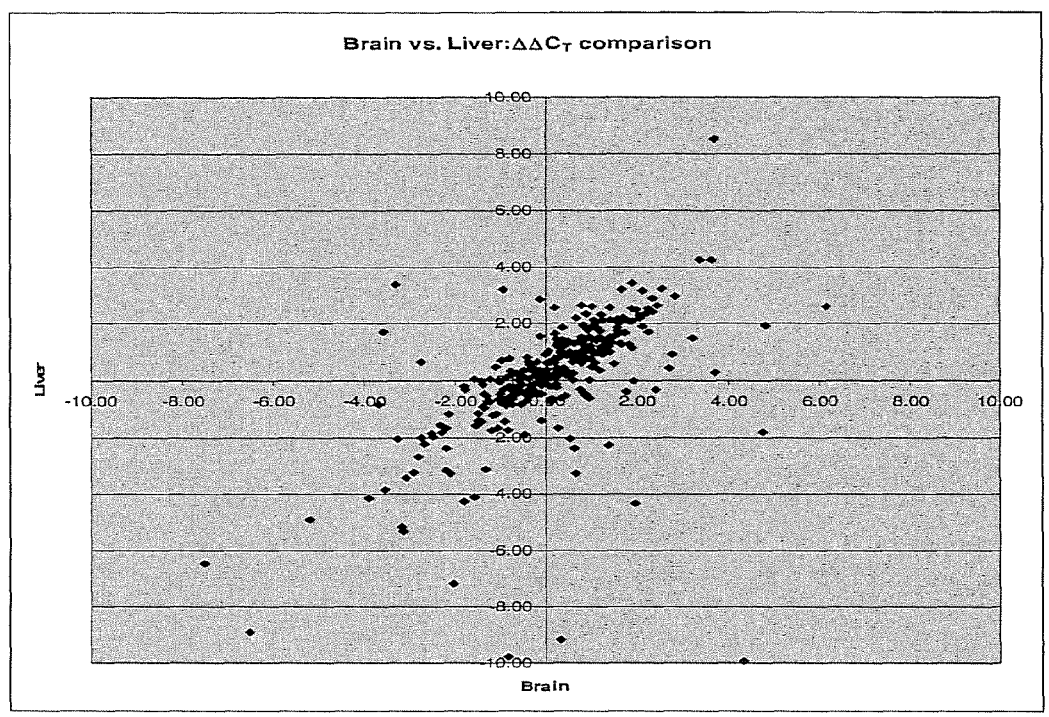
FIG. 4 is a graph exemplifying a $\Delta\Delta C_T$ comparison of a brain and a liver sample.

In various embodiments, a value for $\Delta\Delta C_T T_xS_A$ can be zero or close to zero, which can indicate that there is no bias in the preamplification of target DNA $T_x$. In various embodiments, a negative $\Delta\Delta C_T T_xS_A$ value can indicate the preamplification process was less than 100% efficient for a given target DNA ($T_x$). For example, when using an IVT preamplification process, a percentage of target DNA with a $\Delta\Delta C_T$ of +/−1 $C_T$ of zero can be ~50%, as shown in FIG. 3. In another example, when using a multiplex preamplification process, a percentage of target DNA with a $\Delta\Delta CT$ of +/−1 $C_T$ of zero can be ~90%, as shown in FIG. 4.

Figure 5:
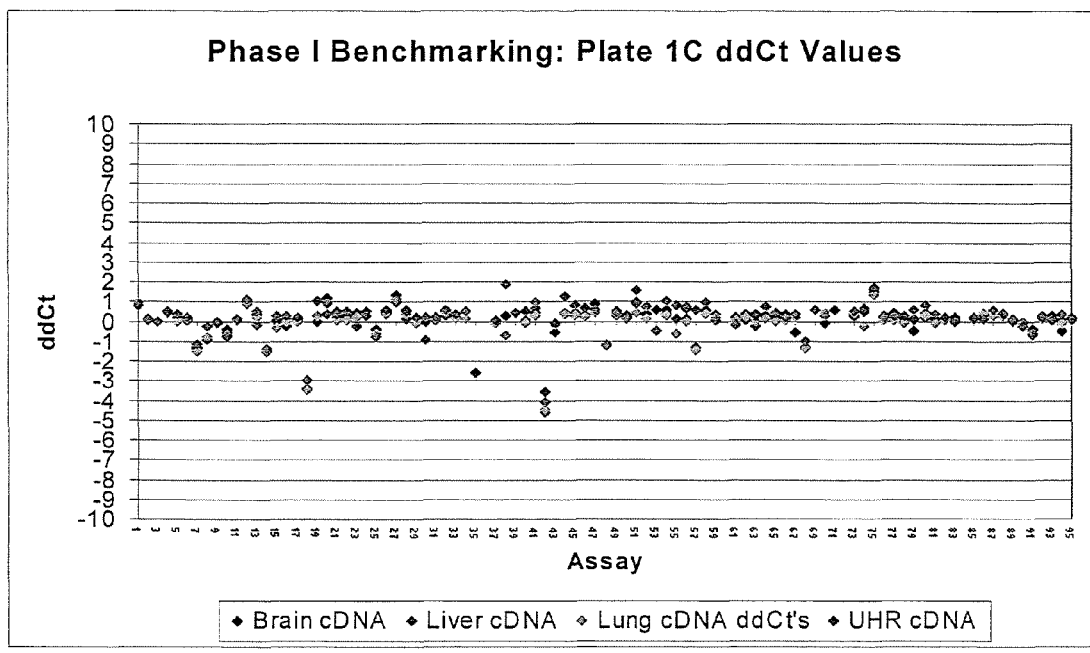
FIG. 5 is a graph exemplifying a $\Delta\Delta C_T$ comparison between four different sample inputs.

In various embodiments, an amplification efficiency can be less than 100% for a particular target DNA, therefore $\Delta\Delta C_T$ is less than zero for the particular target DNA. An example, as shown in FIG. 5, can be an evaluation of $\Delta\Delta C_T$ values for a group of target DNA from a 1536-plex for the multiplex preamplification process including four different human sample input sources: liver, lung, brain and an universal reference tissue composite. In this example, most $\Delta\Delta C_T$ values are near zero, however, some of the target DNA have a negative $\Delta\Delta C_T$ value but these negative values are reproducible from one sample input source to another. In various embodiments, a gene expression analysis system can determine if a bias exists for target DNA analyzed for different sample inputs.

In various embodiments of the present teachings, a gene expression analysis system can use $\Delta\Delta C_T$ values computed for the same target DNA but in different samples (Sample A ($S_A$) and Sample B ($S_B$)) in order to determine the accuracy of subsequent relative expression computations. This results in the equation, $$\Delta\Delta\Delta C_T T_x = \Delta\Delta C_T T_xS_A - \Delta\Delta C_T T_xS_B$$

In various embodiments a value for $\Delta\Delta\Delta C_T T_x$ can be zero or reasonably close to zero which can indicate that the preamplified $\Delta C_T$ values for $T_x$ ($\Delta C_T$ preamplified $T_xS_A$ and $\Delta C_T$ preamplified $T_xS_B$) can be used for relative gene expression computation between different samples via a standard relative gene expression calculation.

Figure 6:
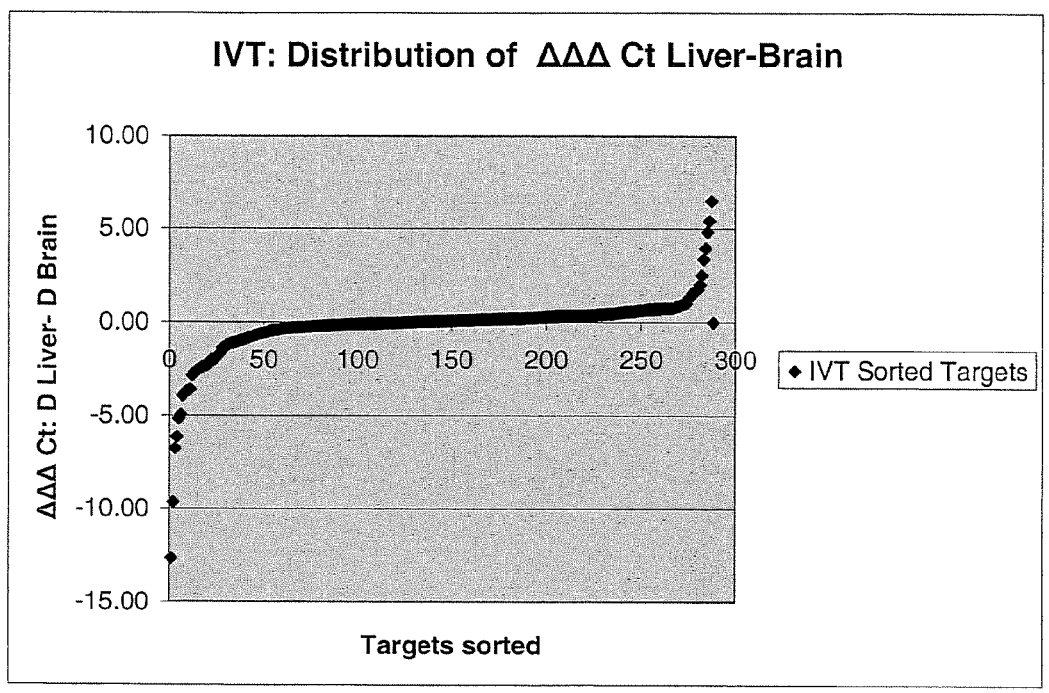
FIG. 6 is a graph exemplifying a $\Delta\Delta\Delta C_T$ of a liver and a brain sample with IVT preamplification.
Figure 7:
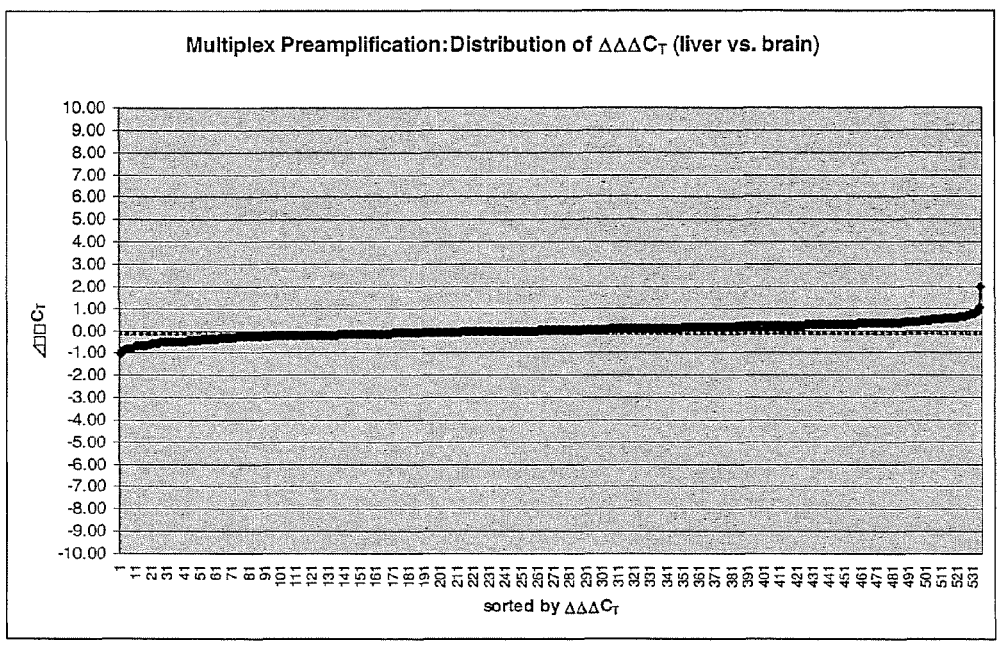
FIG. 7 is a graph exemplifying a $\Delta\Delta\Delta C_T$ of a liver and a brain sample with multiplex preamplification.

In some embodiments, a standard relative gene expression calculation can determine the amount of the target DNA. In some embodiments, a standard relative gene expression calculation employs a comparative $C_T$. In various embodiments, the above methods can be practiced during experimental design and once the conditions have been optimized so that the $\Delta\Delta\Delta C_T T_x$ is reasonably close to zero, subsequent experiments only require the computation of the $\Delta C_T$ value for the preamplified reactions. In various embodiments, $\Delta\Delta C_T T_xS_A$ values can be stored in a database or other storage medium. In such embodiments, these values can then be used to convert $\Delta\Delta C_{T\ preamplified} T_x S_A$ values to $\Delta\Delta C_{T\ not\ preamplified} T_x S_A$ values. In such embodiments, the $\Delta\Delta C_{T\ preamplified} T_x S_y$ values can be mapped back to a common domain. In various embodiments, a not preamplified domain can be calculated using other gene expression instrument platforms such as, for example, a microarray. In various embodiments, the $\Delta\Delta C_T$ $T_x S_A$ values need not be stored for all different sample source inputs ($S_A$) if it can be illustrated that the $\Delta\Delta C_{T\ preamplified} T_x$ is reasonably consistent over different sample source inputs. For example, a distribution of $\Delta\Delta\Delta C_T$ for two different sample inputs (liver and brain) are shown in FIG. 6 (IVT preamplification) and FIG. 7 (multiplex preamplification).

In various embodiments, gene expression can be assessed with microarray technology, which can provide a measure of the cellular concentration of different mRNAs. In some embodiments, a microarray can be a piece of glass or plastic on which single stranded pieces of DNA are affixed in a microscopic array as probes. In some embodiments, thousands of identical probes can be affixed at each point in the array which can make effective detectors.

Typically arrays can be used to detect the presence of mRNAs that may have been transcribed from different genes and which encode different proteins. The RNA can be extracted from many cells, ideally from a single cell type, then converted to cDNA. In various embodiments, the cDNA may be amplified in quantity by PCR. Fluorescent tags can be enzymatically incorporated into the or can be chemically attached to strands of cDNA. In various embodiments, a cDNA molecule that contains a sequence complementary to one of the probes will hybridize via base pairing to the point at which the complementary probes are affixed. In such embodiments, the point on the array can then fluoresce when examined using a microarray scanner. In some embodiments, the intensity of the fluorescence can be proportional to the number of copies of a particular mRNA that were present and thus roughly indicates the activity or expression level of that gene.

In various embodiments, a microarray can be, for example, a cDNA array, a hybridization array, a DNA microchip, a high density sequence oligonucleotide array, or the like. In various embodiments, a microarray can be available from a commercial source such as, for example, Applied Biosystems, Affymetrix, Agilent, Illumina, or Xeotron. In various embodiments, a microarray can be made by any number of technologies including printing with fine-pointed pins onto glass slides, photolithography using pre-made masks, photolithography using dynamic micromirror devices, or ink-jet printers. The lack of standardization in microarrays can present an interoperability problem in bioinformatics, since it can limit the exchange of array data.

In various embodiments, microarray output data can be in a format of fluorescence intensity and in other embodiments, microarray output data may be in a format of chemiluminescence intensity. In various embodiments, an intensity value from a microarray output data can be globally normalized. In some embodiments, told difference values can be determined by subtracting background noise and normalizing the array signal intensity, then dividing experimental sample signal intensity by a control sample signal intensity yielding net sample intensity. In some embodiments, a control sample used to generate the control sample signal intensity can be, for example, Stratagene®, UHR or the like. In some embodiments, a full difference can be converted to a $\log_2$ by the following equation:

$$2^{\Delta\Delta C_T} = 3.3 \log_{10} (\text{net intensity sample 1/net intensity sample 2})$$

In such embodiments, microarray output data is in a $\Delta\Delta C_T$ format. In some embodiments, microarray output data can be converted into a $\Delta\Delta C_T$ format by the following equation:

$$R = (\tfrac{1}{2})^{\Delta\Delta C_T}$$

where R is the resulting measurement from a microarray. Such calculations are available commercially, such as GeneSpring from Silicon Genetics. Other embodiments include converting microarray output data into a $\Delta\Delta C_T$ format using a Global Pattern Recognition (GPR) algorithm which can convert intensity values generated from microarrays from linear values to algorithmic values and can use transformed intensity cutoffs to effect gene and normalizer filters. In such embodiments, GPR, a software algorithm for gene expression analysis is available from The Jackson Laboratory. In various embodiments, microarray output data can be in a standard language or format such as MAGE-ML (microarray and gene expression markup language), MAML (microarray markup language), or MIAME (minimum information about microarray experiments). In various embodiments, such standardized formats and language can be converted to a $\Delta\Delta C_T$ format.

Figure 8:
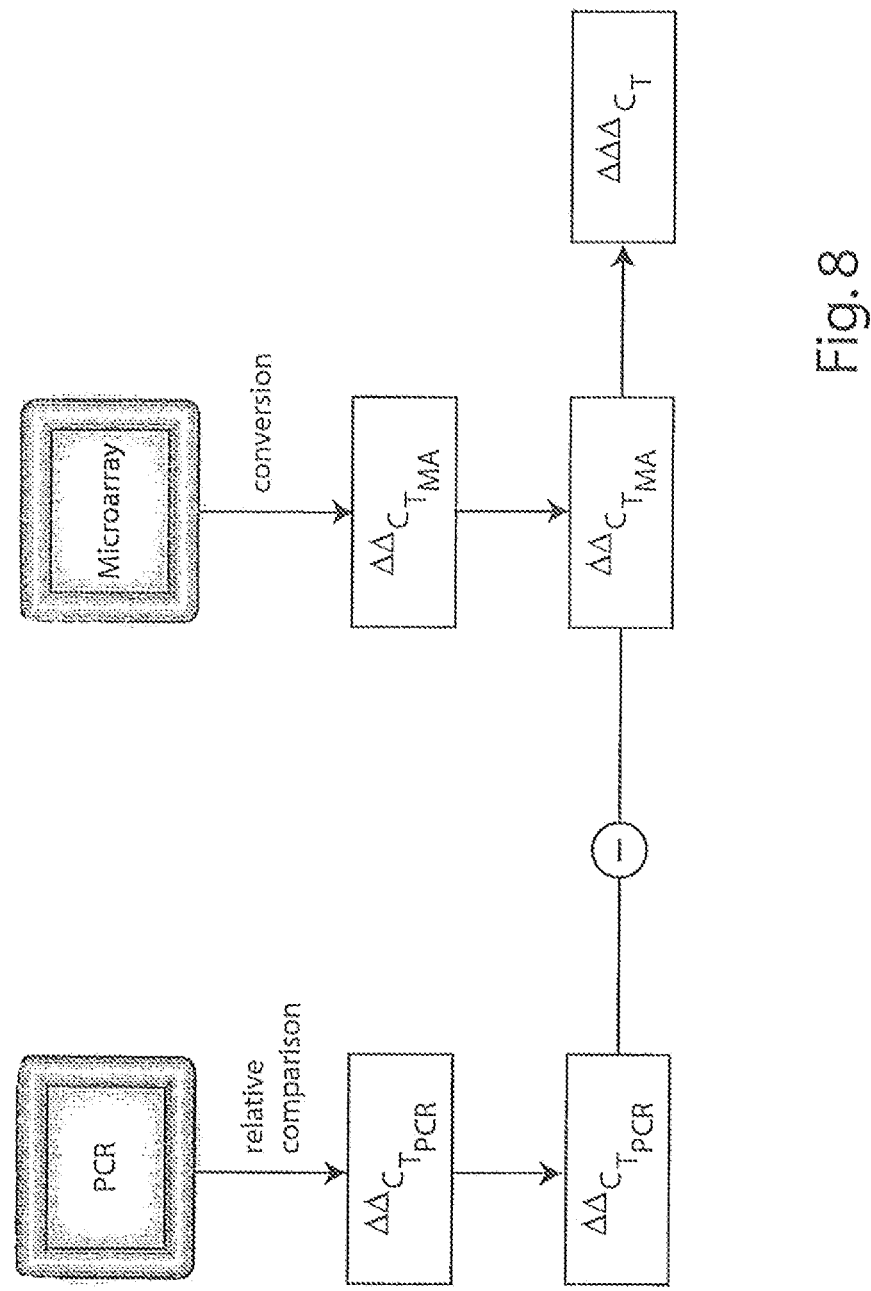
FIG. 8 is a flowchart illustrating a process for determining bias between two gene expression platforms.

In various embodiments, after microarray output data is in a $\Delta\Delta C_T$ format, then real-time PCR data can be directly compared to data from microarray platforms as shown in FIG. 8. In various embodiments, a $\Delta\Delta\Delta C_T$ calculation can be a validation tool to confirm that relative quantitation data can be compared from one amplification/detection process to another. In various embodiments, $\Delta\Delta\Delta C_T$ calculation can be a validation tool to confirm that relative quantitation data can be compared from one sample input source to another sample input source, for example, comparing a sample from liver to a sample from brain in the same individual. In various embodiments, $\Delta\Delta\Delta C_T$ calculation can be a validation tool to confirm that relative quantitation data can be compared from one high-density sequence detector system to another high-density sequence detection system. In various embodiments, $\Delta\Delta\Delta C_T$ calculation can be a validation tool to confirm that relative quantitation data can be compared from one platform to another, for example, data from real time PCR to data from a hybridization array is especially valuable for cross-platform validation. In various embodiments, real time PCR and hybridization array data can be directly compared. In various embodiments, a TaqMan $\Delta\Delta C_T$ can be compared to a microarray output converted to the $\Delta\Delta C_T$ format. In such embodiments, the resultant $\Delta\Delta\Delta C_T$, if within $+/-1$ $C_T$ of zero, can determine a high-degree of confidence that the actual fold difference observed within each of the two platforms is correlative.

In various embodiments, a correction, which can be a quantity added to a calculated or observed value to obtain the true value, may be used so that data generated on two different platforms can be used together in further calculations and analysis. Such embodiments allow for larger and sometimes more complete data sets to be used in gene expression studies. In some embodiments, the correction can be calculated from a resulting $\Delta\Delta\Delta C_T$. In various embodiments, a correction can be a bias correction.

What is claimed is:

1. A method for cross-instrument platform comparison of gene expression data, the method comprising:
   receiving, at a processor of a gene expression analysis system, first cycle threshold data sets from a first instrument platform, wherein the first cycle threshold data sets are for at least one of a first sample, a first reference, and a first calibrator data set, and wherein the first instrument platform is a PCR polynucleotide amplification platform;

receiving, at the processor of the gene expression analysis system, second cycle threshold data sets from a second instrument platform, wherein the second cycle threshold data sets are for at least one of a second sample, a second reference, and a second calibrator data set; and wherein the second instrument platform is a microarray platform;

calculating, by the processor of the gene expression analysis system, a first $\Delta C_T$ given for a first sample data set from the first instrument platform given by:

$$\Delta C_{Tfirst} = C_{Tq\,first} - C_{Tendo\,first},$$

wherein $C_{Tq\,first}$ is a threshold cycle for a first sample data set, and $C_{Tendo\,first}$ is a threshold cycle for a first reference data set;

calculating, by the processor of the gene expression analysis system, a first $\Delta C_T$ given for a first calibrator data set from the first instrument platform given by:

$$\Delta C_{Tcb\,first} = C_{Tq\,cb\,first} - C_{Tendo\,first},$$

wherein $C_{Tq\,cb\,first}$ is a threshold cycle for a first calibrator data set, and $C_{Tendo\,first}$ is a threshold cycle for a first reference data set;

calculating, by the processor of the gene expression analysis system, a second $\Delta C_T$ for a second sample data set from the second instrument platform given by:

$$\Delta C_{Tsecond} = C_{Tq\,second} - C_{Tendo\,second};$$

wherein $C_{Tq\,second}$ is a threshold cycle for a second sample data set, and $C_{Tendo\,second}$ is a threshold cycle for a second reference data set;

calculating, by the processor of the gene expression analysis system, a second $\Delta C_T$ for a second calibrator set from the second instrument platform given by:

$$\Delta C_{Tcb\,second} = C_{Tq\,cb\,second} - C_{Tendo\,second};$$

wherein $C_{Tq\,cb\,second}$ is a threshold cycle for a second calibrator data set, and $C_{Tendo\,second}$ is a threshold cycle for a second reference data set;

calculating, by the processor of the gene expression analysis system, a first $\Delta\Delta C_T$ for the first instrument platform given by;

$$\Delta\Delta C_{Tfirst} = \Delta C_{Tfirst} - \Delta C_{Tcb\,first},$$

calculating, by the processor of the gene expression analysis system, a second $\Delta\Delta C_T$ for the second instrument platform given by $$\Delta\Delta C_{Tsecond} = \Delta C_{Tq\,second} - \Delta C_{Tcb\,second},$$

determining, by the processor of the gene expression analysis system, a measure of preamplifaction or amplification bias within the first sample data set and within the second sample data set to produce an indication of bias across the first and second instrument platforms, wherein the measure of preamplifaction or amplification bias across the first and second instrument platforms is given by, $$\Delta\Delta\Delta C_T = \Delta\Delta C_{Tfirst} - \Delta\Delta C_{Tsecond}; \text{ and}$$

outputting, by the processor of the gene expression analysis system, the measure of preamplifaction or amplification bias across the first and second instrument platforms to a view or report of an analysis session.

2. The method of claim 1, wherein the first sample data set and the second sample data set are based on the same target DNA.

3. The method of claim 1, wherein PCR polynucleotide amplification platform is one of the group consisting of: quantitative PCR, real time quantitative PCR, qualitative PCR, and multiplexed PCR.

4. The method of claim 1, wherein the microarray platform is one of the group consisting of: a hybridization array, a DNA microchip, or a high-density sequence oligonucleotide array.

5. The method of claim 1, wherein the first reference and the second reference are each independently an endogenous reference or a passive internal reference.

6. The method of claim 1, wherein the first reference and the second reference are the same.

7. The method of claim 1, wherein the data obtained from a microarray is converted into a $\Delta\Delta CT$ format using the equation:

$$R = (1/2)^{\Delta\Delta C_T};$$

wherein R is the resulting measurement from the microarray.

* * * * *